US00PP32657P3

(12) United States Plant Patent
Hofmann

(10) Patent No.: US PP32,657 P3
(45) Date of Patent: Dec. 15, 2020

(54) ***NEMESIA* PLANT NAMED 'INNEMCRARE'**

(50) Latin Name: ***Nemesia hybrida* Vent.**
Varietal Denomination: INNEMCRARE

(71) Applicant: Silvia Hofmann, Mainz (DE)

(72) Inventor: Silvia Hofmann, Mainz (DE)

(73) Assignee: INNOVAPLANT ZIERPFLANZEN GmbH + Co. KG, Gensingen (DE)

( * ) Notice: Subject to any disclaimer, the term of this patent is extended or adjusted under 35 U.S.C. 154(b) by 0 days.

(21) Appl. No.: 16/873,437

(22) Filed: Apr. 11, 2020

(65) Prior Publication Data

US 2020/0329617 P1 Oct. 15, 2020

(30) Foreign Application Priority Data

Apr. 15, 2019 (CA) ..... PBR 19-9765

(51) Int. Cl.
*A01H 5/02* (2018.01)
*A01H 6/00* (2018.01)

(52) U.S. Cl.
USPC ..... Plt./458
CPC ..... *A01H 6/00* (2018.05); *A01H 5/02* (2013.01)

(58) Field of Classification Search
USPC ..... Plt./263.1, 458
See application file for complete search history.

*Primary Examiner* — Susan McCormick Ewoldt
*Assistant Examiner* — Karen M Redden
(74) *Attorney, Agent, or Firm* — C. A. Whealy

(57) ABSTRACT

A new and distinct cultivar of *Nemesia* plant named 'INNEMCRARE', characterized by its upright to outwardly spreading plant habit; moderately vigorous growth habit; freely branching habit; freely flowering habit; long flowering period; red-colored flowers that are sterile; and good summer garden performance.

1 Drawing Sheet

Botanical designation: *Nemesia hybrida* Vent.
Cultivar denomination: 'INNEMCRARE'.

CROSS-REFERENCE TO A RELATED APPLICATION AND STATEMENT REGARDING PRIOR DISCLOSURES BY INVENTOR/APPLICANT

This application claims priority to a Canadian Plant Breeders' Rights application filed on Apr. 15, 2019, application number 19-9765. There have been no offers for sale anywhere in the world prior to the effective filing date of this Application and no accessibility to one of ordinary skill in the art could have been derived from the printed Plant Breeder's Rights documents.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor. Applicant claims a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Nemesia* plant, botanically known as *Nemesia hybrida* Vent. and hereinafter referred to by the name 'INNEMCRARE'.

The new *Nemesia* plant is a product of a planned breeding program conducted by the Inventor in Gensingen, Germany.

The objective of the breeding program is to create new semi-upright and freely branching *Nemesia* plants with good summer garden performance.

The new *Nemesia* plant originated from a cross-pollination made by the Inventor in August, 2016 in Gensingen, Germany of a proprietary selection of *Nemesia* Vent. identified as code number N 05 82-1, not patented, as the female, or seed, parent with a proprietary selection of *Nemesia* Vent. identified as code number N 16 95-16, not patented, as the male, or pollen, parent. The new *Nemesia* plant was discovered and selected by the Inventor as a single flowering plant from within the progeny of the stated cross-pollination in a controlled environment in Gensingen, Germany in April, 2017.

Asexual reproduction of the new *Nemesia* plant by terminal vegetative cuttings in a controlled environment in Gensingen, Germany since April, 2017, has shown that the unique features of this new *Nemesia* plant are stable and reproduced true to type in successive generations.

SUMMARY OF THE INVENTION

Plants of the new *Nemesia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'INNEMCRARE'. These characteristics in combination distinguish 'INNEMCRARE' as a new and distinct *Nemesia* plant:

1. Upright to outwardly spreading plant habit.
2. Moderately vigorous growth habit.

3. Freely branching habit.
4. Freely flowering habit.
5. Long flowering period.
6. Red-colored flowers that are sterile.
7. Good summer garden performance.

Plants of the new *Nemesia* differ primarily from plants of the female parent selection in flower color as flowers of plants of the new *Nemesia* are red in color whereas flowers of plants of the female parent selection are white in color.

Plants of the new *Nemesia* differ primarily from plants of the male parent selection in summer performance as plants of the new *Nemesia* flower more freely and continuously during the summer than plants of the male parent selection.

Plants of the new *Nemesia* can be compared to plants of *Nemesia hybrida* 'Intrairedtwo', disclosed in U.S. Plant Pat. No. 23,061. In side-by-side comparisons, plants of the new *Nemesia* differ primarily from plants of 'Intrairedtwo' in the following characteristics:

1. Plants of the new *Nemesia* are more freely branching than plants of 'Intrairedtwo'.
2. Flowers of plants of the new *Nemesia* resist fading whereas flowers of plants of 'Intrairedtwo' fade with development.
3. Plants of the new *Nemesia* flower more freely, continuously and uniformly during the summer than plants of 'Intrairedtwo'.

Plants of the new *Nemesia* can also be compared to plants of *Nemesia hybrida* 'Nesia Burgundy', not patented. In side-by-side comparisons, plants of the new *Nemesia* differ primarily from plants of 'Nesia Burgundy' in the following characteristics:

1. Plants of the new *Nemesia* are larger than plants of 'Nesia Burgundy'.
2. Flowers of plants of the new *Nemesia* are lighter red in color than flowers of plants of 'Nesia Burgundy'.
3. Plants of the new *Nemesia* flower more freely, continuously and uniformly during the summer than plants of 'Nesia Burgundy'.

BRIEF DESCRIPTION OF THE PHOTOGRAPHS

The accompanying colored photographs illustrate the overall appearance of the new *Nemesia* plant showing the colors as true as it is reasonably possible to obtain in colored reproductions of this type. Colors in the photographs may differ slightly from the color values cited in the detailed botanical description which accurately describe the colors of the new *Nemesia* plant. At the top of the photographic sheet (FIG. 1) is a side perspective view of a typical flowering plant of 'INNEMCRARE' grown in a container and at the bottom of the photographic sheet is a close-up view of a typical flowering plant of 'INNEMCRARE'.

DETAILED BOTANICAL DESCRIPTION

The aforementioned photographs and following observations and measurements describe plants grown during the spring in 15.25-cm containers in a polyethylene-covered greenhouse in St. Thomas, Ontario, Canada and under cultural practices typical of commercial *Nemesia* production. During the production of the plants, day temperatures averaged 27° C. and night temperatures averaged 17° C. Plants were pinched when the rooted cuttings were planted and were eight weeks from planting rooted cuttings when the photographs and description were taken. In the following description, color references are made to The Royal Horticultural Society Colour Chart, 2007 Edition, except where general terms of ordinary dictionary significance are used.

Botanical classification: *Nemesia* Vent. 'INNEMCRARE'.

Parentage:

*Female, or seed, parent.*—Proprietary selection of *Nemesia* Vent. identified as code number N 05 82-1, not patented.

*Male, or pollen, parent.*—Proprietary selection of *Nemesia* Vent. identified as code number N 16 95-16, not patented.

Propagation:

*Type.*—By terminal vegetative cuttings.

*Time to initiate roots, summer.*—About ten days at temperatures about 20° C.

*Time to initiate roots, winter.*—About two weeks at temperatures about 20° C.

*Time to produce a rooted young plant, summer.*—About two weeks at temperatures about 20° C.

*Time to produce a rooted young plant, winter.*—About two to three weeks at temperatures about 20° C.

*Root description.*—Fine, fibrous; typically white in color, actual color of the roots is dependent on substrate composition, water quality, fertilizer type and formulation, substrate temperature and physiological age of roots.

*Rooting habit.*—Freely branching; dense.

Plant description:

*Plant and growth habit.*—Herbaceous annual; upright to outwardly spreading; moderately vigorous growth habit; rapid growth rate; freely branching habit; about eight primary branches each with about twelve secondary laterals developing per plant.

*Plant height, soil level to top of foliar plane.*—About 10.4 cm.

*Plant height, soil level to top of floral plane.*—About 19.2 cm.

*Plant diameter.*—About 42.9 cm.

Lateral branch description:

*Length.*—About 25.5 cm.

*Diameter.*—About 3 mm.

*Internode length.*—About 1.9 cm.

*Strength.*—Moderately strong.

*Aspect.*—Mostly upright to outwardly and curving upright.

*Texture and luster.*—Ridged; sparsely to moderately pubescent; matte.

*Color, developing.*—Close to 144A to 144B.

*Color, developed.*—Close to 138A.

Leaf description:

*Arrangement.*—Opposite, simple; sessile.

*Length.*—About 3.6 cm.

*Width.*—About 1.4 cm.

*Shape.*—Lanceolate.

*Apex.*—Narrowly acute.

*Base.*—Obtuse.

*Margin.*—Dentate.

*Texture and luster, upper surface.*—Smooth, glabrous; slightly glossy.

*Texture and luster, lower surface.*—Smooth, glabrous; matte.

*Venation pattern.*—Pinnate; arcuate.

*Color*.—Developing leaves, upper and lower surfaces: Close to 143C. Fully expanded leaves, upper surface: Close to 137A; venation, close to 144A. Fully expanded leaves, lower surface: Close to 147C; venation, close to 144A.

Flower description:

*Flower arrangement and habit*.—Bilabiate single flowers arranged in terminal racemes; flowers develop acropetally towards the apex; flowers face mostly outwardly; freely flowering habit with about 18 flowers per inflorescence and more than 1,200 flowers per plant during the flowering season.

*Fragrance*.—Moderate; floral, pleasant.

*Natural flowering season*.—Long flowering period, in Ontario, plants flower from spring until autumn; flowering continuous during this period; plants begin flowering about seven weeks after planting rooted cuttings.

*Flower longevity*.—Flowers last about three to four days on the plant; flowers not persistent.

*Inflorescence height*.—About 17.5 cm.

*Inflorescence diameter*.—About 5 cm.

*Flower size*.—About 2.3 cm by 2.1 cm.

*Flower depth*.—About 1.6 cm.

*Flower buds*.—Length: About 1.3 cm. Diameter: About 6 mm. Shape: Oval with a short spur. Texture and luster: Moderately pubescent; matte. Color: Close to 53B to 53C.

*Petals*.—Arrangement: Five petals; two upper and two lateral petals fused at base to form an upright lobed and arched upper or banner lip; lower petal modified into a large lower lip with convex oval protuberance and short nectar spur. Spur length: About 7 mm. Spur diameter: About 1.5 mm. Spur texture and luster: Smooth, glabrous; matte. Spur color: Close to 2A; streaks, close to 187C. Length: Upper petals: About 9 mm. Lateral petals: About 9 mm. Lower petal: About 9 mm. Width: Upper petals: About 6 mm. Lateral petals: About 9 mm. Lower petal: About 1.8 cm. Shape: Upper and lateral petals: Obovate. Lower petal: Roughly cordate. Apex, upper and lower petals: Broadly acute to rounded. Apex, lower petal: Emarginate. Margin, upper and lower petals: Entire; not undulate. Margin, lower petal: Entire, slightly undulate. Texture and luster, all petals, upper and lower surfaces: Smooth, glabrous; matte. Color, upper and lateral petals: When opening and fully opened, upper surface: Close to 46C; venation, close to 46C; color becoming closer to N57A with development. When opening and fully opened, lower surface: Close to 51A; venation, close to 51A; color becoming closer to 53D with development. Color, lower petal: When opening, upper surface: Close to 45B. When opening, lower surface: Close to 51A. Fully opened, upper surface: Close to 46C; towards the throat, close to 45A and center, close to N163D; venation, close to 46C; color becoming closer to N57A with development. Fully opened, lower surface: Close to 51A; venation, close to 51A; color becoming closer to 53D with development. Color, throat: Close to 17A; distally, close to 2C.

*Sepals*.—Arrangement: Calyx star-shaped with five sepals fused at the base. Length: About 4 mm. Width: About 2 mm. Shape: Elliptic. Apex: Acute. Margin: Entire. Texture and luster, upper and lower surfaces: Slightly to moderately pubescent; matte. Color, upper surface: Close to 137B. Color, lower surface: Close to 146B.

*Peduncles*.—Length: About 4 cm. Diameter: About 2.5 mm. Angle: Upright to outwardly. Strength: Moderately strong. Texture and luster: Sparsely to moderately pubescent; matte. Color: Close to 147B.

*Pedicels*.—Length: About 1.6 cm. Diameter: About 7 mm. Angle: About 30° to 45° from peduncle axis. Strength: Moderately strong. Texture and luster: Moderately pubescent; matte. Color: Close to 144B.

*Reproductive organs*.—Stamens: Quantity: Four per flower. Filament length: About 2.5 mm. Filament color: Close to 155C. Anther length: Less than 1 mm. Anther shape: Elliptic. Anther color: Close to 157D. Pollen amount: Scarce. Pollen color: Close to 13A to 13B. Pistils: Quantity: One per flower. Pistil length: About 1 mm. Style length: Less than 0.5 mm. Style color: Close to 157D. Stigma diameter: Less than 1 mm. Stigma shape: Oval. Stigma color: Close to 157D. Ovary color: Close to 144C.

*Seeds and fruits*.—Flowers of plants of the new *Nemesia* are sterile and seed and fruit development have not been observed on plants of the new *Nemesia*.

Pathogen & pest resistance: To date, plants of the new *Nemesia* have not been observed to be resistant to pathogens and pests common to *Nemesia* plants.

Garden performance: Plants of the new *Nemesia* have been observed to have good summer garden performance and to tolerate wind and rain and temperatures ranging from about 5° C. to about 30° C.

It is claimed:

1. A new and distinct *Nemesia* plant named 'INNEMCRARE' as illustrated and described.

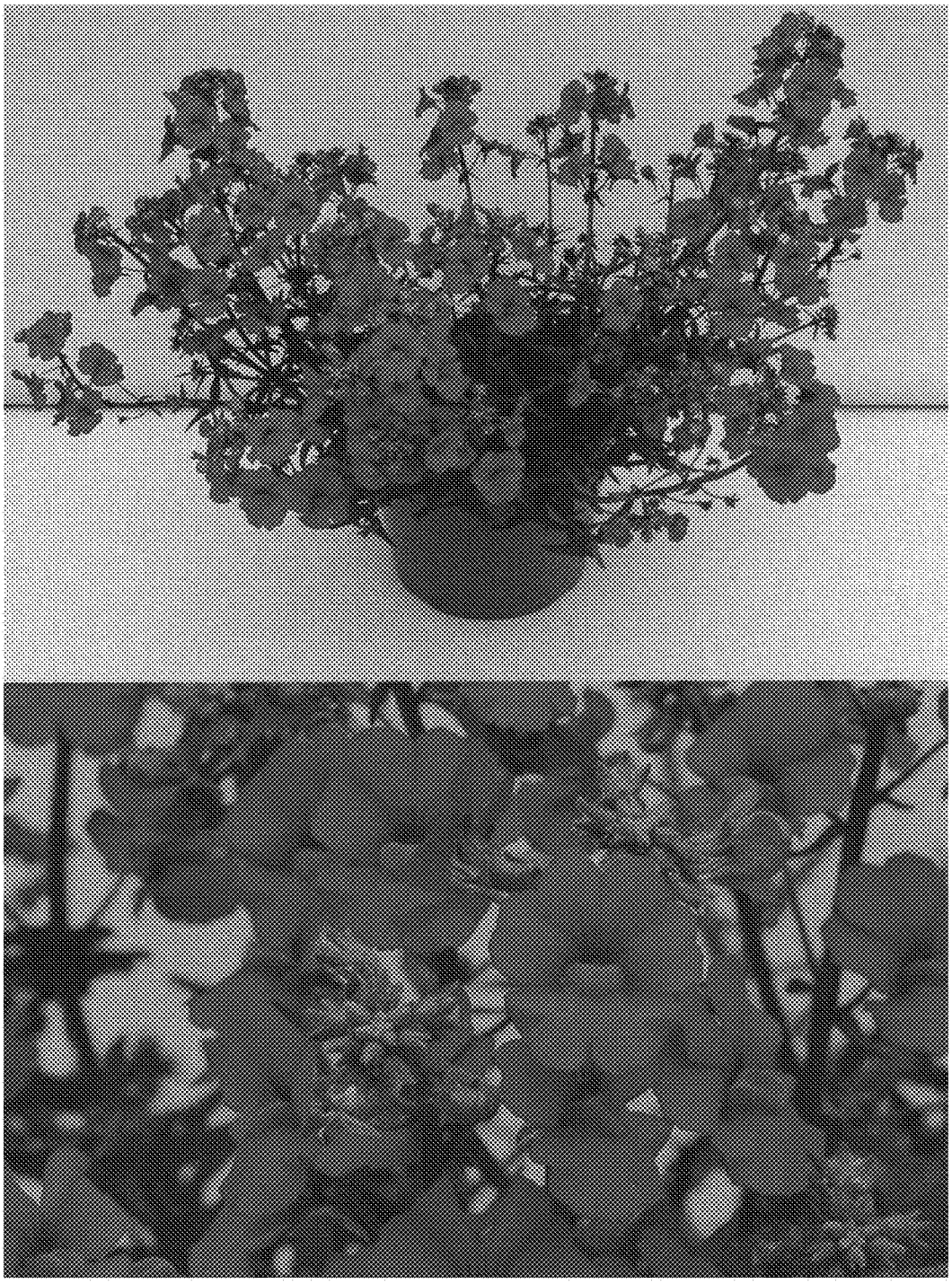

* * * * *